(12) United States Patent
Factor et al.

(10) Patent No.: US 12,329,733 B2
(45) Date of Patent: *Jun. 17, 2025

(54) ACETYL-LEUCINE OR A PHARMACEUTICALLY ACCEPTABLE SALT THEREOF FOR IMPROVED MOBILITY AND COGNITIVE FUNCTION

(71) Applicant: INTRABIO LTD., Begbrook (GB)

(72) Inventors: Mallory Factor, London (GB); Michael Strupp, Munich (DE)

(73) Assignee: INTRABIO LTD., Begbrook (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/349,221

(22) Filed: Jul. 10, 2023

(65) Prior Publication Data
US 2023/0346732 A1 Nov. 2, 2023

Related U.S. Application Data

(60) Continuation of application No. 17/247,757, filed on Dec. 22, 2020, now Pat. No. 11,998,518, which is a division of application No. 16/093,780, filed as application No. PCT/GB2017/051090 on Apr. 19, 2017, now Pat. No. 10,905,670.

(30) Foreign Application Priority Data

Apr. 19, 2016 (GB) ..................... 1606834

(51) Int. Cl.
*A61K 31/198* (2006.01)
*A61P 25/28* (2006.01)

(52) U.S. Cl.
CPC ............ *A61K 31/198* (2013.01); *A61P 25/28* (2018.01)

(58) Field of Classification Search
CPC .............................. A61K 31/198; A61P 25/28
See application file for complete search history.

(56) References Cited

U.S. PATENT DOCUMENTS

| | | | |
|---|---|---|---|
| 10,905,670 B2 | 2/2021 | Factor et al. | |
| 11,998,518 B2 * | 6/2024 | Factor | A61P 25/28 |
| 2008/0097606 A1 * | 4/2008 | Cragg | A61F 2/3872 623/14.12 |
| 2008/0214649 A1 | 9/2008 | Yu et al. | |
| 2009/0318555 A1 | 12/2009 | Fabre et al. | |
| 2020/0338034 A1 | 10/2020 | Factor | |

FOREIGN PATENT DOCUMENTS

WO 2008/032222 A2 3/2008

OTHER PUBLICATIONS

Cooper et al. Br J Psychiatry. Sep. 2013; 203(3): 255-264. (Year: 2013).*
Ferrucci et al. Journal of Gerontology A Biol Sci Med Sci, 2016, vol. 71, No. 9, 1184-1194. (Year: 2016).*
Abe et al., "Medium-Chain Triglycerides in Combination with Leucine and Vitamin D Increase Muscle Strength and Function in Frail Elderly Adults in a Randomized Controlled Trial," The Journal of Nutrition, pp. 1017-1026, Apr. 2016.
Brahim et al., "Comparative analysis of pharmacological treatments with N-acetyl-dl-leucine (Tanganil) and its two isomers (N-acetyl-L-leucine and N-acetyl-D-leucine) on vestibular compensation: Behavioral investigation in the cat," European Journal of Pharmacology, vol. 769, pp. 342-349, Nov. 19, 2015.
Bremova et al., "Acetyl-DL-leucine in Niemann-Picktype C: A case series," Neurology, vol. 85, No. 16, pp. 1368-1375, Oct. 20, 2015.
Frances et al., "An anecdotal report by an Oxford basic neuroscientist: effects of acetyl-dl-leucine on cognitive function and mobility in the elderly," Journal of Neurology, vol. 263, No. 6, pp. 1239-1240, Apr. 28, 2016.
International Search Report dated Jul. 26, 2017, in International Application No. PCT/GB2017/051090.
Iwasaki et al., "Dizziness and Imbalance in the Elderly: Age-related Decline in the Vestibular System," Aging and Disease, vol. 6, No. 1, pp. 38-47, Feb. 2, 2015.
Jahn et al., Dizziness and Unstabel Gait in Old Age—Etiology, Diagnosis and Treatment, Deutsches Arzteblatt International Feb. 2013, vol. 112, No. 23, pp. 387-393, Jun. 5, 2015.
Salzman, American Family Physician, Jul. 1, 2010, vol. 82, No. 1, pp. 61-68 (Year 2010).
Strupp et al., "Effects of acetyl-dl-leucine in patients with cerebellar ataxia: a case series," Journal of Neurology, vol. 260, No. 10, pp. 2556-2561, Jul. 9, 2013.
English translation of Office Action in Counterpart Chinese App. No. 201780029480.6 dated Mar. 25, 2021.
Essentials for Prevention and Treatment of Common Diseases in the Elderly, Haizao NI, Second Military Medical University Press, pp. 201-204, published on May 2015.
Regimen Starting from Brain-Invigoration, Li Gao, China Press of Traditional Chinese Medicine, pp. 25-26, published on Mar. 2014.
Strupp, Michael and Arbusow, Viktor, "Acute Vestibulopathy", Current opinion in Neurology 14.1 (2001), pp. 11-20.
Platt, Frances M., et al., "Lysosomal Storage Diseases", Nature Reviews Disease Primers 4.1 (2018), p. 27.
Strupp, Michael and Brandt, Thomas, "Vestibular Neuritis", Seminars in Neurology, vol. 29, No. 05 © Thieme Medical Publishers, 2009.
Wang W., Prevention and Treatment of Geriatric Diseases, Anhui Science and Technology Publishing House, Jun. 1986, 1.Ed., p. 94-95 (Published in Chinese, English translation provided).

* cited by examiner

*Primary Examiner* — Kara R. McMillian
(74) *Attorney, Agent, or Firm* — Finnegan, Henderson, Farabow, Garrett & Dunner, LLP

(57) ABSTRACT

The present disclosure is directed to acetyl-leucine or a pharmaceutically acceptable salt thereof for use in improving cognitive function, mobility, or cognitive function and mobility in a subject, for example, in an elderly subject.

10 Claims, 6 Drawing Sheets

A

B

A

B

A

B

A

B

A

B

ACETYL-LEUCINE OR A PHARMACEUTICALLY ACCEPTABLE SALT THEREOF FOR IMPROVED MOBILITY AND COGNITIVE FUNCTION

This application is a continuation of application of U.S. application Ser. No. 17/247,757, filed Dec. 22, 2020, which is a divisional of U.S. application Ser. No. 16/093,780, filed Oct. 15, 2018, now U.S. Pat. No. 10,905,670, which is a national stage entry under 35 U.S.C. § 371 of International Application No. PCT/GB2017/051090, filed on Apr. 19, 2017, and published as WO 2017/182802 A1, which claims priority to Great Britain Patent Application No. 1606834.8, filed on Apr. 19, 2016; the contents of these applications are each incorporated herein by reference in their entirety.

The present disclosure relates to acetyl-leucine, and pharmaceutically acceptable salts of the same, and specifically to their use to improve mobility and cognitive function, for example in the elderly.

The changes that occur with ageing can lead to problems with a person's ability to move around. Mobility problems may include unsteadiness while walking, difficulty getting in and out of a chair, or falls. Muscle weakness, joint problems, pain, disease and neurological (brain and nervous system) difficulties—common conditions in older people—can all contribute to mobility problems. Sometimes several mild problems occur at one time and combine to seriously affect mobility.

In addition to potential mobility problems, all ageing humans will develop some degree of decline in cognitive capacity, symptoms often including forgetfulness, decreased ability to maintain focus, decreased problem-solving capacity and/or reduced spatial awareness. If left unchecked, symptoms can progress into more serious conditions, such as dementia and depression, or even Alzheimer's disease.

Many factors are believed to contribute to age-related cognitive decline, including oxidative stress and free radical damage, chronic low-level inflammation, declining hormone levels (like estrogen, testosterone, DHEA and pregnenolone), inner arterial lining (endothelium) dysfunction, insulin resistance, excess body weight, suboptimal nutrition, loneliness, lack of social network and high stress, amongst other things.

Unfortunately, there are few therapeutic options that are currently offered to patients with signs and symptoms of ageing, such as impaired mobility and cognitive decline. Therefore a need remains for new therapies that could benefit elderly people, by preventing or reducing symptoms such as these.

Furthermore, although impaired mobility and/or cognitive function may be often associated with ageing, such signs may also be observed in any subject that presents with lower baseline levels of mobility and/or cognitive function. There remains a need for new therapies to prevent or reduce such symptoms in subjects suffering therefrom.

The present disclosure provides acetyl-leucine, or a pharmaceutically acceptable salt thereof, for use in a method of improving cognitive function, mobility, or cognitive function and mobility in a subject.

In one embodiment, there is provided acetyl-leucine, or a pharmaceutically acceptable salt thereof, for use in a method of improving cognitive function in a subject. In another embodiment, there is provided acetyl-leucine, or a pharmaceutically acceptable salt thereof, for use in a method of improving mobility in a subject.

In a further embodiment, the subject is an elderly subject.

Further, there is provided acetyl-leucine, or a pharmaceutically acceptable salt thereof, for use in a method of improving mobility and/or cognitive function in an elderly subject.

In another embodiment, there is provided a method of improving mobility and/or cognitive function in an elderly subject, the method comprising administering a therapeutically effective amount of acetyl-leucine, or a pharmaceutically acceptable salt thereof, to the subject.

In one embodiment, the cognitive function is one or more selected from the group consisting of perception, memory, creation of imagery, awareness, reasoning, thinking and capacity for judgment.

According to the present disclosure, acetyl-leucine or pharmaceutically acceptable salt thereof may be used to treat an age-related decrease in cognitive function and/or mobility.

In one embodiment, the acetyl-leucine is used in a dose of between 1.5 g and 10 g, for example between 4 g and 10 g per day. In another embodiment, the acetyl-leucine is used in a dose of more than 4 g to no more than 6 g per day.

The dose of acetyl-leucine may be administered, for example, across two or more administrations. In one embodiment, the dose of acetyl-leucine is administered across three administrations.

In one embodiment, the method comprises administering the acetyl-leucine for a treatment duration of two weeks or more. In another embodiment, the method comprises administering the acetyl-leucine for a treatment duration of seven weeks or more.

In one embodiment, the method comprises administering the acetyl-leucine in a dose of between 1.5 g and 10 g, for example between 4.5 g and 10 g per day, taken across three administrations per day, for a treatment duration of two months or more.

In one embodiment, the subject is a well elderly subject. The subject may be otherwise healthy, except for an impairment of mobility and/or cognitive function where the mobility and/or cognitive function has reduced as the subject has aged i.e. reduced due to the aging process.

In one embodiment, the subject does not have vertigo, and/or a neurological and/or neurodegenerative disease, disorder or condition. In one embodiment, the subject does not have vertigo.

In another aspect, the present disclosure provides use of acetyl-leucine, or a pharmaceutically acceptable salt thereof, for improving cognitive function, mobility, or cognitive function and mobility in a subject.

In another aspect, the present disclosure provides a method of improving cognitive function, mobility, or cognitive function and mobility in a subject, the method comprising administering a therapeutically effective amount of acetyl-leucine, or a pharmaceutically acceptable salt thereof, to the subject.

In another aspect, the present disclosure provides use of acetyl-leucine, or a pharmaceutically acceptable salt thereof, for the manufacture of a medicament for improving cognitive function, mobility, or cognitive function and mobility in a subject.

DESCRIPTION

Figure 1:
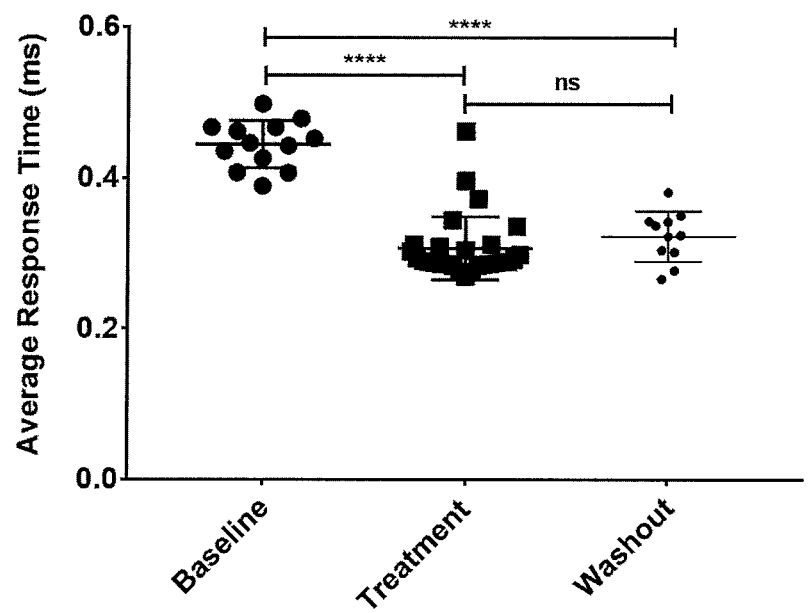
FIG. 1 illustrates the Psychomotor Vigilance Task performance during baseline and treatment period. (A) Data is presented as mean±SD of n=13 (Baseline), 28 (Treatment) or 11 (washout) daily measurements, ****–p<0.0001. Determination of statistical significance was performed via 1-way ANOVA with Tukey's correction. (B) Each individual data point is an average of the 10 trials that make up a daily test (mean±SD, n=10). Dashed line indicates division between baseline/on-medication/washout periods.
Figure 1:
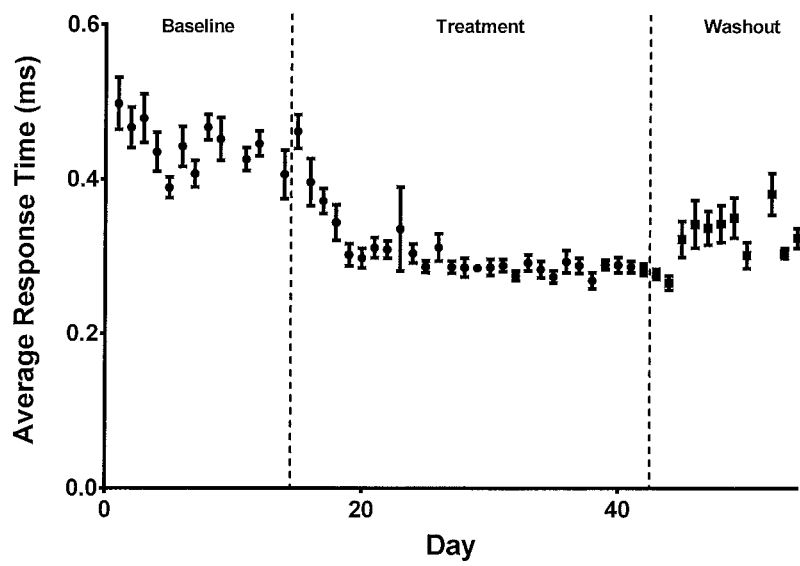

It has been found, according to the present disclosure, that acetyl-leucine (N-acetyl-leucine), or a pharmaceutically acceptable salt of the same improves mobility and cognitive function. In particular, it has been found, according to the present disclosure, that acetyl-leucine, or a pharmaceutically acceptable salt of the same, improves mobility and cognitive function in the elderly.

Acetyl-leucine in racemate form and salts of the same are known for their effectiveness in the treatment of vertigo of various origins, notably Meniere's vertigo and vertigo of inflammatory (vestibular neuritis) or toxic origin.

Acetyl-leucine is marketed by Pierre Fabre Medicament in racemate form as an anti-vertigo medicament under the tradename Tanganil®. Clinical results relating to said medicament reported by various authors demonstrate an improvement in vertigo symptomology in more than 95% of cases, including the disappearance of vertigo attacks.

Acetyl-DL-leucine has been used in France to treat acute vertigo since 1957. Despite numerous hypotheses, including stabilisation of membrane potential, its pharmacological and electrophysiological modes of action remain unclear (1,2). A FDG-μPET study in a rat model of an acute unilateral labyrinthectomy (3) showed a significant effect of an L-enantiomer N-acetyl-L-leucine on postural compensation by activation of the vestibulo-cerebellum and a deactivation of the posterolateral thalamus (4). Improvement of cerebellar symptoms in a case series with cerebellar patients of different etiologies has been observed (5). However, another case series did not find benefit (6). In a third recent case series in 12 patients with Niemann-Pick type C this agent caused improvement in ataxic symptoms (7). Further, a PET study in patients with cerebellar ataxia of different etiologies given acetyl-DL-leucine demonstrated an increased metabolism in the midbrain and lower brainstem in responders (8), which could explain the benefits observed.

Surprisingly, the inventors show that acetyl-leucine can also be used to benefit the elderly who, other than displaying the normal signs of ageing, may be in good health. Specifically, it has been found that acetyl-leucine can improve mobility and cognitive function in the elderly. This was entirely unexpected, as such benefits had not been observed, and could not have been deduced, from the prior art teaching.

The present inventors show that acetyl leucine can be used to treat subjects that have disorders distinct from ataxia (e.g. distinct from disorders such as cerebellar ataxia and Niemann Pick), and distinct from vertigo. For example, the subjects treated by the present disclosure may be otherwise healthy, except that they have an impairment of mobility where the mobility has been impaired due to the ageing process. The finding that the acetyl-leucine can be used to treat non-vertiginous disorders was surprising.

Consequently, the present disclosure provides acetyl-leucine, or a pharmaceutically acceptable salt of the same, for use in a method of improving mobility and/or cognitive function in an elderly subject.

The acetyl-leucine may be in racemic form, which means that the compound comprises about equal amounts of enantiomers. Alternatively it may be present in an enantiomeric excess of either the L-enantiomer or the D-enantiomer. In one embodiment, the acetyl-leucine is present in an enantiomeric excess of the L-enantiomer. The racemic and enantiomeric forms may be obtained in accordance with known procedures in the art.

A "pharmaceutically acceptable salt" as referred to herein, is any salt preparation that is appropriate for use in a pharmaceutical application. Pharmaceutically acceptable salts include, but are not limited to, amine salts, such as N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine, tris(hydroxymethyl)aminomethane and the like; alkali metal salts, such as lithium, potassium, sodium and the like; alkali earth metal salts, such as barium, calcium, magnesium and the like; transition metal salts, such as zinc, aluminum and the like; other metal salts, such as sodium hydrogen phosphate, disodium phosphate and the like; mineral acids, such as hydrochlorides, sulfates and the like; and salts of organic acids, such as acetates, lactates, malates, tartrates, citrates, ascorbates, succinates, butyrates, valerates, fumarates and the like.

"Mobility" refers to the ability of a subject to move. Mobility may be assessed in the elderly using one or more simple tests. As illustrated in the Examples, the "get up and go" test is a simple test capable of measuring mobility. In this test, the speed of sit to stand and walking to a target point is analysed, suitably as described in the Examples. For example, the test may begin with the subject sitting in a chair. At the start of the stop clock, the subject should rise unaided and walk to a target point. The target point may be 2-10 m away, optionally 4-6 m away. The stop clock should be stopped upon the subject reaching the target point. Any change in mobility, for example, over time or through treatment, can be monitored by using the "get up and go" test at two or more time points and comparing the results, again as illustrated in the Examples. Other suitable tests for measuring mobility include those used in the Elderly Mobility Scale (EMS), a 20-point validated assessment tool for the assessment of frail elderly subjects (9), considering locomotion, balance and key position changes.

The phrase "improving mobility", as referred to herein, means a positive change in the ability of the subject to move. The positive change can be measured using any of the aforementioned tests on two or more occasions, for example, a first occasion to measure baseline mobility and a second occasion to measure mobility following a period of time (in which treatment may have been administered). The more confident the subject feels due to improved steadiness (with treatment, for example) the more rapidly s/he completes the test. Mobility could be said to be improved when at least a about 5% increase in performance in the relevant test, between two time points, is observed. For example, an increase in performance of at least about 10%, at least about 15%, at least about 20%, at least about 25%, at least about 30%, at least about 40%, at least about 50%, at least about 60%, at least about 70%, at least about 80%, at least about 90% or at least about 100% in the relevant test, between the two time points, is observed. Further for example, an increase in performance of at least 5%, at least 10%, at least 15%, at least 20%, at least 25%, at least 30%, at least 40%, at least 50%, at least 60%, at least 70%, at least 80%, at least 90% or at least 100% in the relevant test, between the two time points, is observed. The two time points may be one week apart, two weeks apart, three weeks apart, four weeks apart, two months apart, three months apart, four months apart, five months apart or even six months apart. Treatment may be administered during the intervening period. Thus, as an example, "improving mobility" can mean that the subject will demonstrate an at least about 5% increase in speed from a baseline measurement, as measured using the "get up and go" test as defined herein. For example, the subject may demonstrate an increase in speed in this test of at least about 10%, at least about 15%, at least about 20%, at least about 25%, at least about 30%, at least about 40%, at least about 50%, at least about 60%, at least about 70%, at least about 80%, at least about 90% or at least about 100%. Further for example, the subject may demonstrate an increase in speed in this test of at least 5%, at least 10%, at least 15%, at least 20%, at least 25%, at least 30%, at least 40%, at least 50%, at least 60%, at least 70%, at least 80%, at least 90% or at least 100%.

In one embodiment, the subject has a mobility disorder associated with ageing.

The term "mobility disorder associated with ageing" as used herein refers to an impairment in mobility that is a direct consequence of the ageing process; this is in contrast with an impairment in mobility that is not a direct consequence of the ageing process. Clinical presentation may differ between subjects with a mobility disorder associated with ageing and subjects with impairment in mobility that is not a direct consequence of the ageing process, for example subjects with ataxia. Ataxia may present as a subject slaloming during walking, while a mobility disorder associated with ageing may present as an increased propensity to falls. Thus, for example, cerebellar ataxia is not a mobility disorder associated with ageing.

In addition to the mobility assessments disclosed above, mobility in a subject having a mobility disorder associated with ageing may be tested, for example, using assessments of balance and/or through monitoring the number of falls experienced by the subject.

According to the present disclosure, acetyl-leucine or pharmaceutically acceptable salt thereof may be used to improve balance in a subject, wherein the subject has impaired balance associated with ageing. According to the present disclosure, the impaired balance associated with ageing is not vertigo.

According to the present disclosure, the subject may, for example, not have benign paroxysmal positional vertigo (BPPV); vestibular neuritis; vertigo related to Meniere's disease, Wallenberg's syndrome, cerebellar ischemia, perilymph fistula or acoustic neurinoma; or recurring vertigo of traumatic or toxic origin.

According to the present disclosure, acetyl-leucine or pharmaceutically acceptable salt thereof may be used to treat balance disorder associated with ageing.

According to the present disclosure, acetyl-leucine or pharmaceutically acceptable salt thereof may be used to increase a subject's stability, for example when standing and/or walking, wherein the subject has decreased stability associated with ageing.

According to the present disclosure acetyl-leucine or pharmaceutically acceptable salt thereof may be used to reduce a subject's unsteadiness whilst walking, wherein the subject has increased unsteadiness associated with ageing.

According to the present disclosure, acetyl-leucine or pharmaceutically acceptable salt thereof may be used to treat a subject with impaired gait wherein the impaired gait is associated with ageing. The subject may have senile gait disorder.

According to the present disclosure, acetyl-leucine or pharmaceutically acceptable salt thereof may be used to increase gait velocity and or cadence in a subject wherein the subject has impaired gait velocity and or cadence associated with ageing.

According to the present disclosure, acetyl-leucine or pharmaceutically acceptable salt thereof may be used to treat a subject that has a pre-disposition to falls, wherein the pre-disposition to falls is associated with ageing "Cognitive function" can mean any mental process that involves a symbolic operation, for example, perception, memory, creation of imagery, awareness, reasoning, thinking and capacity for judgment. Measures of cognitive functioning include assessment tools designed to measure, for example: (a) general intelligence, (b) nonverbal intelligence, (c) achievement, (d) attention/executive functioning, (e) memory and learning, (f) visual-motor and motor functioning and (g) language. Such assessment tools are well-known in the art and include, for example, Wechsler Adult Intelligence Scale and Woodcock-Johnson III Tests of Cognitive Abilities (both for assessing general intelligence), Raven Progressive Matrices (for assessing nonverbal intelligence), Wide Range Achievement Test and Woodcock-Johnson III Tests of Achievement (for assessing academic achievement), Conners' Continuous Performance Test II (for assessing attention/executive functioning), Wide Range Assessment of Memory and Learning (for assessing memory and learning), Bender Visual-Motor Gestalt Test, Halstead-Reitan Grip Strength Test, Halstead-Reitan Finger Tapping Test and Lafayette Grooved Pegboard Task (all for assessing visual-motor and motor functioning) and Peabody Picture Vocabulary Test (for assessing language).

Cognitive function may also be assessed using reaction speed and/or alertness tests, such as the Psychomotor Vigilance Task (e.g. as disclosed in the Examples). This test assesses components including fine motor skills; psychomotor speed; lapses of attention; instability of alertness; and impulsivity induced by fatigue.

For example, the Psychomotor Vigilance Task (PVT) is a sustained-attention, reaction-timed task that measures the speed with which subjects respond to a visual stimulus. The subject monitors a screen and presses the screen as quickly as possible upon the appearance of visual stimuli. The visual stimuli will then disappear and reappear (at irregular time intervals) e.g., 10 times over the course of the test, with the subject touching the screen as quickly as possible upon each reappearance. Test performance is quantified from an average of the e.g. 10 reaction times.

Any change in cognitive function, for example, over time or through treatment, can be monitored by using one or more of these well-established tests at two or more time points and comparing the results.

The phrase "improving cognitive function", as referred to herein, means a positive change in the ability of the subject to perform a symbolic operation, for example, to perceive, remember, create a mental image, have clarity of thought, be aware, to reason, think or judge. The positive change can be measured using any of the aforementioned tests on two or more occasions, for example, a first occasion to measure baseline cognitive function and a second occasion to measure cognitive function following a period of time (in which treatment may have been administered). Cognitive function could be said to be improved when at least about a 5% increase in performance in the relevant test, between two time points, is observed. For example, an increase in performance of at least about 10%, at least about 15%, at least about 20%, at least about 25%, at least about 30%, at least about 40%, at least about 50%, at least about 60%, at least about 70%, at least about 80%, at least about 90% or at least about 100% in the relevant test, between the two time points, is observed. Further for example, an increase in performance of at least 5%, at least 10%, at least 15%, at least 20%, at least 25%, at least 30%, at least 40%, at least 50%, at least 60%, at least 70%, at least 80%, at least 90% or at least 100% in the relevant test, between the two time points, is observed. The two time points may be one week apart, two weeks apart, three weeks apart, four weeks apart, two months apart, three months apart, four months apart, five months apart or even six months apart. Treatment may be administered during the intervening period. Thus, as an example, "improving cognitive function" can mean that the subject will demonstrate an at least about 5% increase in performance from a baseline measurement, as measured using the well-established Wechsler Adult Intelligence Scale. For example, the subject may demonstrate an increase in performance in this test of at least about 10%, at least about 15%, at least about 20%, at least about 25%, at least about 30%, at least about 40%, at least about 50%, at least about 60%, at least about 70%, at least about 80%, at least about 90% or at least about 100%. Further for example, the subject may demonstrate an increase in performance in this test of at least 5%, at least 10%, at least 15%, at least 20%, at least 25%, at least 30%, at least 40%, at least 50%, at least 60%, at least 70%, at least 80%, at least 90% or at least 100%.

According to the present disclosure, acetyl-leucine or pharmaceutically acceptable salt thereof may be used to increase reaction speed, for example the speed in which a subject responds to a visual stimulus.

In one embodiment, the subject has a decrease in cognitive function associated with ageing.

The term "decrease in cognitive function associated with ageing" as used herein refers to a decrease in cognitive function that is a direct consequence of the ageing process; in contrast with a decrease in cognitive function that is not a direct consequence of the ageing process. Clinical presentation may differ between subjects with a decrease in cognitive function associated with ageing and subjects with decrease in cognitive function that is not a direct consequence of the ageing process.

The term "improving" may encompass treating and/or ameliorating any impaired mobility and/or cognitive decline in the subject. An age-related decrease in mobility and/or cognitive function may thus be partially or wholly reversed using acetyl-leucine as described herein.

Also envisaged and encompassed by the present disclosure is the prevention of impaired mobility and/or cognitive decline in the elderly, using acetyl-leucine as described herein. Thus, an age-related decrease in mobility and/or cognitive function may never occur at all, using acetyl-leucine as described herein.

The acetyl-leucine, or a pharmaceutically acceptable salt of the same, may be formulated and administered to a subject, for example to an elderly subject, in accordance with known teachings in the art.

The acetyl-leucine, or a pharmaceutically acceptable salt of the same, may thus be formulated as a pharmaceutical composition, optionally comprising a pharmaceutically acceptable carrier.

The active agent (composition) may be used as a monotherapy (i.e. use of the active agent alone) for improving mobility and/or cognitive function in subject, such as an elderly subject. Alternatively, the active agent (composition) may be used as an adjunct to, or in combination with, known therapies for improving mobility and/or cognitive function in a subject, for example in an elderly subject.

The active agent (composition) may take any of a number of different forms depending, for example, on the manner in which it is to be used. Thus, for example, the agent or composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the carrier of the pharmaceutical composition according to the invention should be one which is well-tolerated by the subject to whom it is given.

A "pharmaceutically acceptable carrier" as referred to herein, is any known compound or combination of known compounds that are known to those skilled in the art to be useful in formulating pharmaceutical compositions.

In a further embodiment, the pharmaceutically acceptable carrier may be a solid, and the composition may be in the form of a powder or tablet. A solid pharmaceutically acceptable carrier may include, but not limited to, one or more substances which may also act as flavouring agents, buffers, lubricants, stabilisers, solubilisers, suspending agents, wetting agents, emulsifiers, dyes, fillers, glidants, compression aids, inert binders, sweeteners, preservatives, dyes, coatings, or tablet-disintegrating agents. The carrier may also be an encapsulating material. In powders, the carrier is a finely divided solid that is in admixture with the finely divided active agents according to the present disclosure. In tablets, the active agent may be mixed with a carrier having the necessary compression properties in suitable proportions and compacted in the shape and size desired. The powders and tablets, for example, contain up to 99% of the active agents. Suitable solid carriers include, for example, calcium phosphate, magnesium stearate, talc, sugars, lactose, dextrin, starch, gelatin, cellulose, polyvinylpyrrolidine, low melting waxes and ion exchange resins. In another embodiment, the pharmaceutically acceptable carrier may be a gel and the composition may be in the form of a cream or the like.

In yet a further embodiment, the carrier may include, but is not limited to, one or more excipients or diluents. Examples of such excipients are gelatin, gum *arabicum*, lactose, microcrystalline cellulose, starch, sodium starch glycolate, calcium hydrogen phosphate, magnesium stearate, talcum, colloidal silicon dioxide and the like.

However, in another embodiment, the pharmaceutically acceptable carrier may be a liquid, and the pharmaceutical composition is in the form of a solution. Liquid carriers are used in preparing solutions, suspensions, emulsions, syrups, elixirs and pressurized compositions. The active agent according to the present disclosure may be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid carriers for oral and parenteral administration include water (partially containing additives as above, e.g. cellulose derivatives, such as sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurised compositions can be a halogenated hydrocarbon or other pharmaceutically acceptable propellant.

Liquid pharmaceutical compositions, which are sterile solutions or suspensions, can be utilised by, for example, intramuscular, intrathecal, epidural, intraperitoneal, intravenous and subcutaneous injection. The active agent may be prepared as a sterile solid composition that may be dissolved or suspended at the time of administration using sterile water, saline, or other appropriate sterile injectable medium.

The agents and compositions of the present disclosure may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The agents used according to the disclosure can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Acetyl-leucine and compositions comprising the same may alternatively be administered by inhalation (e.g. intranasally). Compositions may also be formulated for topical use. For instance, creams or ointments may be applied to the skin.

Acetyl-leucine according to the present disclosure may be incorporated within a slow- or delayed-release device. Such devices may, for example, be inserted on or under the skin, and the medicament may be released over weeks or even months. Such devices may be used when long-term treatment with acetyl-leucine used according to the present disclosure is required and which would normally require frequent administration (e.g. at least daily administration).

In one embodiment, the pharmaceutical composition is in the form of a tablet. In tablets, the active agent may be mixed with a vehicle having the necessary compression properties in suitable proportions and compacted in the shape and size desired. The tablets may contain up to 99% by weight of the active agents.

Thus, in one embodiment, the acetyl-leucine, or a pharmaceutically acceptable salt of the same, is provided in a solid dosage form suitable for oral administration, notably in the form of a tablet.

Pharmaceutical formulations in solid oral dosage form, such as tablets, may be prepared by any method known in the art of pharmacy. Pharmaceutical formulations are usually prepared by mixing the active substance, or a pharmaceutically acceptable salt thereof, with conventional pharmaceutically acceptable carriers, diluents or excipients.

A tablet may be formulated precisely as is known in the art. Tanganil®, for example, includes wheat starch, pregelatinised maize (corn) starch, calcium carbonate and magnesium stearate as excipients. The same, or similar, excipients may be employed in the present disclosure.

The precise composition of each 700 mg Tanganil® tablet is as follows: 500 mg acetyl-DL-leucine, 88 mg wheat starch, 88 mg pregelatinised maize (corn) starch, 13 mg calcium carbonate and 11 mg magnesium stearate. The same tablets may be employed in the present disclosure.

A generic version of such tablets may alternatively be used.

The acetyl-leucine, or a pharmaceutically acceptable salt of the same, may be administered at a dose between 500 mg and 10 g per day, preferably between 1.5 g and 10 g per day (for example between 1 g and 10 g, 2 g and 10 g, 3 g and 10 g, 4 g and 10 g, 1 g and 5 g, 2 g and 5 g, 3 g and 5 g, or 4 g and 5 g per day), optionally by solid oral or liquid oral route. Tanganil®, for example, is prescribed for adults in a dose of 1.5 g to 2 g per day for the symptomatic treatment of episodes of vertigo, i.e. 3-4 tablets in two doses, morning and evening. Under this prescription, the treatment duration varies according to clinical progression (from 10 days to 5 or 6 weeks). At the start of treatment, or in the event of failure, the dosage may be safely increased up to 3 g or even 4 g per day.

In accordance with the present disclosure, acetyl-leucine, or a pharmaceutically acceptable salt of the same, may be administered at a dose that is higher than previously known and/or for a treatment duration that is longer than previously known.

For example, the administered dose may be between 4 g and 10 g per day, such as between 4.5 g and 10 g per day. It may be between 5, 5.5, 6, 6.5, 7, 7.5, 8, 8.5, 9 or 9.5 g and 10 g per day. It may be more than 4 g per day, but less than 10, 9.5, 9, 8.5, 8, 7.5, 7, 6.5, 6, 5.5 or 5 g per day. For example, a dose may be in the range of more than 4 g to no more than 6 g per day, such as in the range of more than 4 g to no more than 5 g per day, for example further ranging from 4.25 g to 4.75 g per day. In a further embodiment, these doses are administered in a solid oral dosage form, notably tablets. In another embodiment, these doses are for acetyl-leucine when in its racemic form. Doses for acetyl-leucine when an enantiomeric excess is present may be lower than those recited here, for example, around 50% lower. The above recited dose-ranges when halved are thus also explicitly encompassed by the disclosure.

The total daily dose may be spread across multiple administrations, e.g. administration may be required two or more times a day to achieve the required dose. As an example, the required number of tablets to provide the total daily dose of acetyl-leucine may be split across two administrations (for example, in the morning and evening) or three administrations (for example, in the morning, noon and evening). Each dose is suitably administered with food. Thus, as an example, a total daily dose of 4.5 g acetyl-DL-leucine may be administered as three Tanganil® (or equivalent) tablets with breakfast, three further tablets with lunch and three further tablets with dinner.

The treatment duration may vary according to clinical progression. It may be seven days or more, two weeks or more, three weeks or more, one month or more, six weeks or more, seven weeks or more or two months or more. For example, it is three months or more, four months or more, five months or more or even six months or more.

Any and all combinations of dosage form, dose amount, dosing schedule and treatment duration are envisaged and encompassed by the disclosure. An example combination is a total daily dose of between 4.5 g and 10 g per day, taken across three administrations per day, for a treatment duration of two months or more. A further example combination is a total daily dose of more than 4 g to no more than 5 g per day, taken across three administrations per day, for a treatment duration of six months or more. The dosage form may be, for example, a solid oral dosage form, notably tablets.

Treatment may commence upon, for example, observation of mobility impairment and/or cognitive impairment in a subject.

Treatment may commence upon, for example, observation of mobility impairment and/or cognitive impairment in an elderly subject.

A "subject", as used herein, may be a vertebrate, mammal or domestic animal. Hence, compositions according to the disclosure may be used to treat any mammal, for example livestock (e.g. a horse), pets, or may be used in other veterinary applications. Further for example, the subject is a human.

"Elderly", as used herein, may refer to subjects of advanced age. For example, it can refer to men and women aged 70 or over, 75 or over, 80 or over, 85 or over or 90 or over. Non-human subjects in the corresponding later years of life are also encompassed by this term.

The elderly subject may be a well elderly subject, i.e., other than displaying the normal signs of ageing, the subject is in good health. In one embodiment, the subject does not have vertigo or any (clinically presenting) neurological or neurodegenerative disease, disorder or condition. In an alternative embodiment, the elderly subject may have vertigo and/or a (clinically presenting) neurological or neurodegenerative disease, disorder or condition, in addition to the normal signs of ageing.

In accordance with another embodiment, there is provided a method of improving mobility and/or cognitive function in a subject, such as an elderly subject, the method comprising administering a therapeutically effective amount of acetyl-leucine, or a pharmaceutically acceptable salt thereof, to the subject.

A "therapeutically effective amount" of an agent is any amount which, when administered to a subject, is the amount of agent that is needed to produce the desired effect. For example, the therapeutically effective amount of acetyl-leucine used may be between 4 g and 10 g per day, for example between 4.5 g and 10 g per day. Further for example, the amount of agent may be more than 4 g to no more than 5 g per day, and for example from about 4.25 g to 4.75 g per day.

All of the features described herein (including any accompanying claims, abstract and drawings), and/or all of the steps of any method so disclosed, may be combined with any of the above aspects in any combination, except combinations where at least some of such features and/or steps are mutually exclusive.

EXAMPLES

The present disclosure will now be explained in further detail in the following Examples, which demonstrate the utility of acetyl-leucine or a pharmaceutically acceptable salt thereof in improving motility and cognitive function, for example in the elderly.

Example 1

Subject

The subject is a 90-year-old male, and a retired physician with no signs of dementia. He has experienced progressive postural imbalance for five years with no extrapyramidal or cerebellar signs. He has experienced incomplete arousal wakefulness over the past two years but has normal sleep patterns. He had polio in his twenties and has aspects of post-polio syndrome, including partial vocal cord paralysis, muscle weakness and spinal misalignment. He leads an independent active life, reads prolifically and uses a laptop computer to communicate with family. His only medication was glaucoma eye drops at the time of this study.

Initial Treatment

Treatment Protocol

Treatment with acetyl-DL-leucine (Tanganil®) was started because the patient was suffering from imbalance and gait disorder. He initiated a one-month course comprising nine 500 mg tablets taken three times a day (TID) with meals, i.e., a total daily dosage of 4.5 g.

Measurement of Mobility

The ability of the subject to move was measured in a home setting "get up and go test". This test involved the subject rising unaided from his chair and walking the length of his living area to his kitchen. This was timed over seven consecutive days prior to treatment, and over the next seven consecutive days once treatment with Tanganil® had started.

Results

By 7-10 days of treatment the subject was more confident walking due to improved balance. In a home setting "get up and go test" the average time taken for the subject to rise unaided from his chair and walk the length of his living area to his kitchen, prior to Tanganil® treatment, was 40±3 seconds. The average time taken for this once treatment had started was 30±2 seconds. The subject was consistently 25% faster than pre-treatment. He had been struggling to get in and out of bed and that resolved at the same time.

After 2-3 weeks of treatment the subject suddenly described being fully alert on waking and that his mind had cleared. His family noticed a significant improvement in his cognitive function, spatial awareness and general demeanor. He was able to navigate his environment without any of the confusion that had been evident prior to treatment. For example, his house contains numerous doors and, prior to treatment, he often had to stop and think twice about which door to open in order to access a certain room. After treatment this diminished, which was indicative of, inter alia, improved memory.

After one month the subject ceased taking acetyl-DL-leucine. His balance remained good for two weeks then deteriorated, whereas his cognition gradually declined to his pre-treatment status over one month. The "get up and go" test was also similar to his pre-treatment performance level.

Second Treatment

Treatment Protocol

The same subject then initiated another month of treatment, i.e. a further one-month course comprising nine 500 mg capsules taken TID with meals (total daily dosage of 4.5 g).

Results

The improvements the subject had noticed in the first month of treatment rapidly returned.

Further Treatment

Treatment Protocol

The subject now remains on acetyl-DL-leucine (Tanganil®) at a dose of 4.5 g per day.

Results

The improvements the subject had noticed in the first and second months of treatment have continued. The confusion that was evident prior to treatment is now entirely absent.

He has experienced no side effects over eighteen months.

Conclusions

The subject and his family agree that the acetyl-DL-leucine treatment has resulted in significant benefit on multiple neurological systems, in particular mobility and cognitive function, greatly improving his quality of life.

Example 2

The subject is a 75 year old male patient with balance disorder/senile gait disorder and impaired spatial orientation (non-vertiginous dizziness) leading to backward falls. In addition, the subject presents a very discreet symmetric hypokinetic-rigid syndrome.

The subject was diagnosed as having a balance disorder in 2016. Datscan was borderline pathological (i.e. reduction in dopamine receptors indicating possible Parkinson's Disease), however no improvement was observed during treatment with L-Dopa. An MRI on the subject showed unspecific white matter lesions and a slight atrophy of the right motocortex.

Day 0: the patient was started on a treatment regimen of acetyl-DL-leucine 3 gram per day for the first week, followed by 5 gram per day.

Day 14: The subject was subsequently re-evaluated. An improvement of dizziness symptoms was found along with a significant reduction in the frequency of falls. No change of hypokinetic-rigid syndrome was reported.

Day 56: treatment was suspended.

Day 62: The subject was subsequently re-evaluated. The patient reported an increase of dizziness symptoms two days after suspension of treatment (noting the sensation of being drunk).

The study is continuing, with the subject returning to continuous treatment.

Example 3

An 86 year-old male patient was diagnosed with a mild slowly progressive postural imbalance and gait disorder five years earlier. This was described as feeling like a sailor on a ship when walking. From time to time the subject had to use a cane. The subject had no symptoms while sitting or lying. The subject also suffers from atrial fibrillation, and has bilateral hip prostheses.

Clinical examination of the subject revealed slowness of walking with increased body sway. There was evidence for a mild polyneuropathy. There was no evidence for vestibular, ocular motor or cerebellar dysfunction.

Laboratory tests of the vestibular system were normal. Posturography showed increased body sway. Gait analysis revealed small steps and reduced gait velocity. MRI of the brain was normal.

The patient was treated with Tanganil® 500 mg in 3 separate doses throughout the day –1 g upon waking, 1 g prior to lunch and 1 g prior to the evening meal for one week, followed by 2 g upon waking, 1.5 g prior to lunch and 1.5 g prior to the evening meal.

Feedback by the subject's spouse 22 days after beginning treatment with acetyl-leucine indicated a significant reduction of dizziness and imbalance, and significant improvement of gait. Improvement was reported to have begun in the second week of treatment. Medication was well tolerated.

Further tests have not yet been possible due to the subject experiencing an unrelated illness (flu), but treatment is continuing.

Conclusion

Improvement of gait, reduction of dizziness and imbalance was reported by the spouse and the patient.

Example 4

An 89 year-old male patient presented with gait problems and postural imbalance for three years. There were no symptoms while sitting or lying. The course of the symptoms was slowly progressive. The patient had bilateral hearing problems, but otherwise the patient history was unremarkable.

Clinical examination of the patient revealed slowness of walking with increased body sway while standing with the eyes closed. There was no evidence for vestibular, ocular motor or cerebellar dysfunction.

Laboratory tests of the vestibular system (using video head impulse test, caloric irrigation, vestibular evoked myogenic potentials) were normal.

Video of the patient's gait was taken and the gait was quantitatively analysed (results are shown in Table 1).

An MRI of the patient's brain showed a mild subcortical vascular encephalopathy.

The patient was then treated with Tanganil® (500 mg) in 3 separate doses throughout the day –1 g upon waking, 1 g prior to lunch and 1 g prior to the evening meal for one week, followed by 2 g upon waking, 1.5 g prior to lunch and 1.5 g prior to the evening meal.

In a follow-up 3 weeks after beginning acetyl-leucine treatment the patient and his daughter reported that his gait and imbalance was significantly improved. He could get up much easier and more quickly. He also reported climbing stair cases is much easier. Video analysis shows that the patient is now even able to run. The medication was very well tolerated.

Conclusion

Improvement of gait, reduction of dizziness and imbalance during treatment with Tanganil® was reported by the patient and his daughter and further documented by gait analysis and video. The medication was also well tolerated.

The results of quantitative gait analysis before and after treatment are:

TABLE 1

|  | Before treatment | After 3 weeks' treatment | Standard value (±SD) |
| --- | --- | --- | --- |
| Natural walking speed (cm/sec) | 88 | 96 | 88.03 (25.96) |
| Maximum walking speed (cm/sec) | 141 | 157 | 120.79 (31.17) |
| Cadence (steps/minute) | 92 | 100 | 102.89 (4.12) |
| Spreading width (distance between the heel center of one footprint to the line of movement of the other foot) (cm) | 9.3 | 8.1 | 11.79 (3.53) |
| Step cycle length (distance between two consecutive contacts of a foot on the ground) (cm) | 116 | 116 | 102.80 (28.51) |
| % of the time of two periods in the gait cycle in which both feet at the same time are in contact with the ground | 27.2 | 25.5 | 24.33 (2.77) |
| Coefficient of variation (CV) of stride time: CV = (standard deviation/mean) × 100 | 1.6 | 1.8 | 3.25 (1.13) |

In summary, with acetyl-leucine treatment there was:
an increase of self-chosen gait velocity from 88 to 96 cm/sec;
an increase of maximal gait velocity from 141 to 157 cm/sec; and
an increase of so-called cadence (steps per minute) from 92 to 100.

Overall, there was a significant improvement documented by these quantitative measures.

Example 5

A 77 year-old patient experienced progressive gait disorder with small steps and problems with the initiation of gait for more than five years. MRI showed a subcortical vascular encephalopathy (due to arterial hypertension for many years). Datscan revealed a slight reduction of dopamine-receptors. No improvement was observed during treatment with L-Dopa.

Day 0: the patient reported four falls over the previous three months and the patient's spouse reported mild cognitive impairment in the patient. The diagnosis was confirmed with severe reduction of gait velocity and impaired initiation of gait.

Quantitative gait analysis with the "gait-rite" showed a significant reduction of maximal gait velocity (84 cm/sec) and self-chosen gait velocity (55 cm/sec).

The patient was treated with 3 gram per day of acetyl-DL-leucine for two weeks with a considerable improvement of gait reported by the patient and his spouse.

Then medication was stopped with a worsening of symptoms.

Day 28: Re-evaluation revealed an impairment of gait which was documented by video. Treatment with 3 gram per day of acetyl-DL-leucine was started again.

Day 42: In a further re-evaluation the subject's spouse reported a dramatic improvement with impact on functioning and quality of living. It was reported by the spouse that the subject's gait was even better than two years ago. No further falls were reported.

Clinical examination revealed significant improvement of gait and balance, the patient was now even able to run (documented by video).

Quantitative gait analysis showed an increase of maximal gait velocity from 84 cm/sec to 130 cm/sec (running not quantified) and self-chosen gait velocity from 55 cm/sec to 62 cm/sec.

The subject is now undergoing continuous treatment with further follow-up examinations planned.

Example 6

A 59 year-old male patient was diagnosed with a postural imbalance with occasional falls and stumbles (at a frequency of 2-3 per month). His main complaints were experiencing problems going upstairs and downstairs, and problems walking on uneven ground. The subject reported no tendency to fall in a specific direction. The patient has also complained about a slow progressive cognitive decline, especially in terms of short memory and cognitive flexibility. His family members have noticed perseverations and occasional diffuseness in communication with him. Regarding his comorbidities, he was previously diagnosed with insulin-dependent diabetes mellitus, and with thyroxine-substituted hypothyreosis.

The patient was examined clinically by means of the following clinical assessments: maximal distance to walk; timed Up and Go test; Scale for the Assessment and Rating of Ataxia (SARA).

The patient was also examined by means of posturography after 1 month of the therapy with Tanganil® 500 mg (2 g upon waking, 1.5 g prior to lunch and 1.5 g prior to the evening meal). Medication was taken 30 minutes prior to the meal, or at least 2 hours after the meal.

Baseline (prior to commencement of treatment): Maximal distance to walk until the patient could not walk anymore because of fatigue was 1 km. The stance up-and-go test yielded 25.4 sec. SARA yielded 6.5/40. Clinical examination revealed accentuated postural imbalance, with intentional tremor and dysmetria bilaterally. Stance with feet together was possible with increased omnidirectional sway, which was especially pronounced in the dorsoventral and anteroposterior axes. Tandem stance and gait was not possible to perform due to an increased fall risk. Mean timed 8-meter-walking test was 6.5 sec. The tune-fork examination showed a decreased proprioception on the medial malleolus bilaterally.

During treatment with Tanganil® (2 g upon waking, 1.5 g prior to lunch and 1.5 g prior to the evening meal) for 1-month, the following assessments were made:

Objective Measurements: Maximal distance to walk increased to 1.5 km. The stance up-and-go test on medication yielded 21.2 sec. SARA yielded 2/40. The sway previously experienced became visibly calmer. Stance with feet together, as well as tandem stance and gait was possible with increased omnidirectional sway. Mean timed 8-meter-walking test yielded 4.4 sec.

Subjective Measurements: The patient had more energy, was more agile and interactive, especially after the morning dosage. Since the patient was keen on doing DIY in his house and garden, he described that he had more drive to do these activities, was much quicker and more efficient in his daily routine. His family members noticed that he is more coherent in his communication and his executive function improved as well. He was subjectively more postural stable, both when walking and going upstairs and downstairs. He did not have to hold the side rails in order to stabilise himself. Moreover, he did not record any falls during the therapy period of 1 month.

Side effects: Sleepiness was observed under the 2 g/1.5 g/1.5 g per day dosage regimen. The dosage was reduced to 1 g upon waking, 1 g prior to lunch and 1 g prior to the evening meal, daily after 1 month of the treatment. This led to a cease in these side-effect symptoms.

Current state: The improvements disclosed above remained unchanged on the lower dosage medication (1 g/1 g/1 g) for over 4 months. The side effects have not returned. The frequency of falls is currently between 0-1/month.

Example 7

Subject

The subject is a 66-year old male with no apparent dysfunction in cognitive ability or movement/balance.

Study Design

The subject's reaction speed and alertness was assessed using the Mind Metrics App (Psychomotor Vigilance Task, 10 trials per test). The Psychomotor Vigilance Task (PVT) is a sustained-attention, reaction-timed task that measures the speed with which subjects respond to a visual stimulus. The subject is required to monitor a screen and press the screen as quickly as possible upon the appearance of visual stimuli. The visual stimuli will then disappear and reappear (at irregular time intervals) 10 times over the course of the test, with the subject touching the screen as quickly as possible upon each reappearance. Test performance is quantified from an average of the 10 reaction times. The tests were performed daily under comparable conditions. The subject was assessed for 2 weeks prior to taking acetyl-leucine, which constitutes the baseline period.

From Day 15 onwards, the subject took 5 g Acetyl-DL-Leucine (Tanganil® 500 mg, Pierre Fabre) daily. Medication was taken at least 2 hours after and 30 minutes prior to eating. The 5 g daily dose was taken in 3 separate doses throughout the day-2 g upon waking, 1.5 g prior to lunch and 1.5 g prior to the evening meal.

Daily treatments and assessments continued for 4 weeks. The subject then began a 2 week washout period.

Due to reported improvement in balance on treatment we measured balancing ability at the end of the treatment period and at the end of the washout period. This assessment required the subject to close their eyes and lift their non-dominant foot around 6 inches off the ground. The subject was then timed to see how long they could remain upright and without significant wobbles. This was repeated three times, and the values averaged.

Subjective Measurements

The subject reported an improvement in general alertness and a shortening of the time required to go from 'asleep' to 'fully awake'. He also noticed an improvement in his balance.

Objective Measurements

Treatment with 5 g/day Acetyl-DL-Leucine was associated with a significant improvement in Psychomotor Vigilance Task performance, relative to the baseline period (0.444 ms vs 0.307 ms, p<0.0001) (FIG. 1A). Upon beginning treatment at Day 15, test performance began to improve, reaching a new, lower baseline that was maintained from Day 19 until the end of the treatment period (FIG. 1B). After beginning washout there was a notable decrease in test performance (FIG. 1B), although this was not significantly different to the treatment period (0.307 ms (treatment) vs 0.3224 ms (washout), p-0.4747). Test performance during the washout period was also significantly better than in the baseline period (0.322 ms (washout) vs 0.444 ms (baseline), p<0.0001).

Balance was assessed on the last day of the treatment period. The subject was able to remain balanced for 7.27 seconds (average of 3 tests). This test was repeated at the end of the washout period. The length of time subject could remain balanced had decreased to 4.01 seconds (average of 3 tests).

Adverse Events

The subject reported feeling a mild dizziness/lightheadedness on one occasion during the first week on medication. The subject reduced the daily dose from 5 g to 3 g for one day only and reported that the dizziness/lightheadedness abated. The next day the daily dose was increased back to 5 g. It remained at this level for the remainder of the 4 week treatment period, with no recurrence of dizziness or lightheadedness.

Example 8

Subject

The subject is a 29-year old male with no apparent dysfunction in cognitive ability or movement/balance.

Study Design

The subject's reaction speed and alertness was assessed via the Mind Metrics App (Psychomotor Vigilance Task, 10 trials per test). The tests were performed daily under comparable conditions. The subject was assessed for 2 weeks prior to taking acetyl-leucine, which constitutes the baseline period. From Day 15 onwards, the subject took 5 g Acetyl-DL-Leucine (Tanganil® 500 mg, Pierre Fabre) daily. Medication was taken at least 2 hours after and 30 minutes prior to eating. The 5 g daily dose was taken in 3 separate doses throughout the day-2 g upon waking, 1.5 g prior to lunch and 1.5 g prior to the evening meal. Daily treatments and assessments continued for 4 weeks. The subject then began a 2 week washout period.

Subjective Measurements

The subject reported an improvement in general alertness. He also reported a decrease in anxiety, possibly linked to being able to think with a clearer head. He reported no difference in balance.

Objective Measurements

Figure 2:
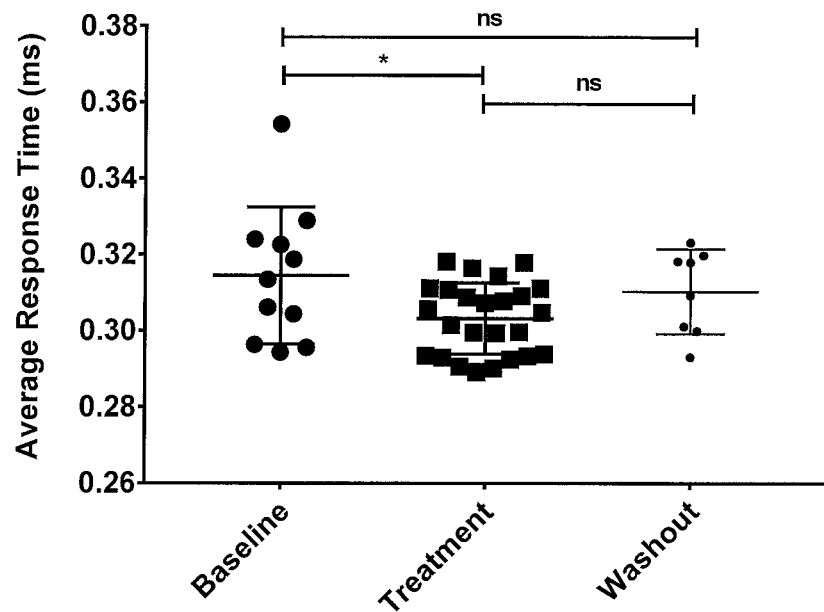
FIG. 2 illustrates the Psychomotor Vigilance Task performance during baseline and treatment period. (A) Data is presented as mean±SD of n=11 (Baseline), 25 (Treatment) or 8 (washout) daily measurements, *–p<0.05. Determination of statistical significance was performed via 1-way ANOVA with Tukey's correction. (B) Each individual data point is an average of the 10 trials that make up a daily test (mean±SD, n=10). Dashed line indicates division between baseline/on-medication/washout periods.
Figure 2:
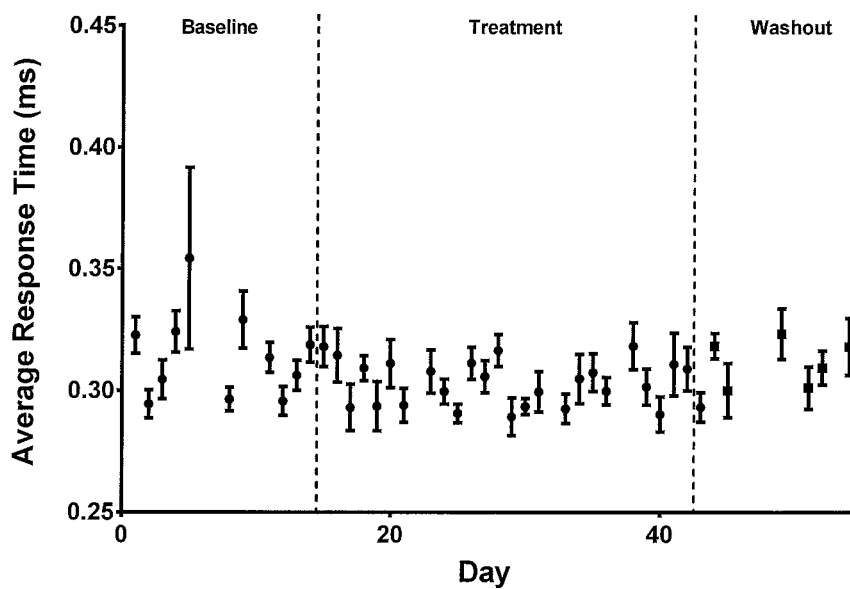

Treatment with 5 g/day Acetyl-DL-Leucine was associated with a small but statistically significant improvement in Psychomotor Vigilance Task performance, relative to the baseline period (0.3145 ms vs 0.3032 ms, p<0.05) (FIG. 2A). Test performance was not significantly different during the washout period from either the baseline or on-treatment values (0.3032 ms vs 0.3145/0.3104 ms respectively).

Adverse Effects

None reported.

Example 9

Subject

The subject is a 55-year old female with no apparent dysfunction in cognitive ability or movement/balance.

Study Design

The subject's reaction speed and alertness was assessed via the Mind Metrics App (Psychomotor Vigilance Task, 10 trials per test). The tests were performed daily under comparable conditions. The subject was assessed for 2 weeks prior to taking acetyl-leucine, which constitutes the baseline period. From Day 15 onwards, the subject took 5 g Acetyl-DL-Leucine (Tanganil® 500 mg, Pierre Fabre) daily. Medication was taken at least 2 hours after and 30 minutes prior to eating. The 5 g daily dose was taken in 3 separate doses throughout the day −2 g upon waking, 1.5 g prior to lunch and 1.5 g prior to the evening meal. Daily treatments and assessments continued for 4 weeks. The subject then began a 2 week washout period.

Balancing ability was measured at the end of the treatment period and at the end of the washout period. This assessment required the subject to close their eyes and lift their non-dominant foot around 6 inches off the ground. The subject was then timed to see how long they could remain upright and without significant wobbles. This was repeated three times, and the values averaged.

Subjective Measurements

The subject reported a shortening of the time required to go from 'asleep' to 'fully awake'. The treatment period coincided with travel for work, and a time difference of 8 hrs.

Objective Measurements

Figure 3:
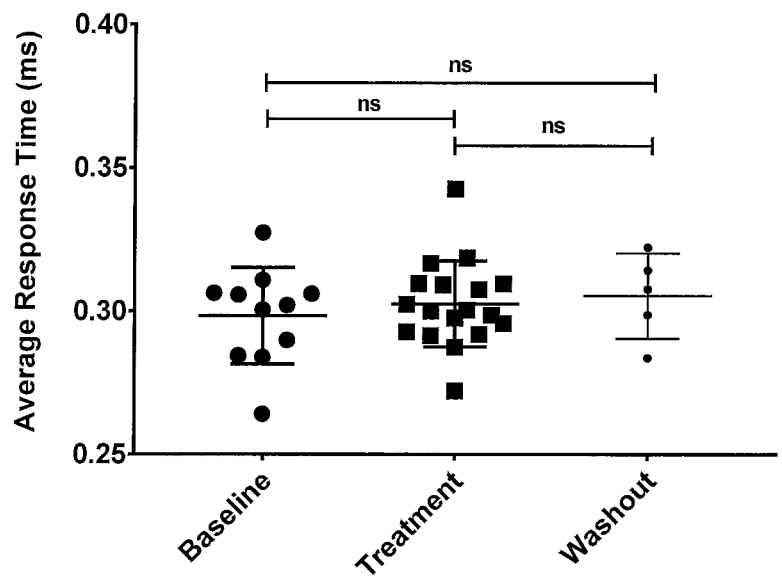
FIG. 3 illustrates the Psychomotor Vigilance Task performance during baseline and treatment period. (A) Data is presented as mean±SD of n=11 (Baseline), 18 (Treatment) or 5 (washout) daily measurements. Determination of statistical significance was performed via 1-way ANOVA with Tukey's correction. (B) Each individual data point is an average of the 10 trials that make up a daily test (mean±SD, n=10). Dashed line indicates division between baseline/on-medication/washout periods.
Figure 3:
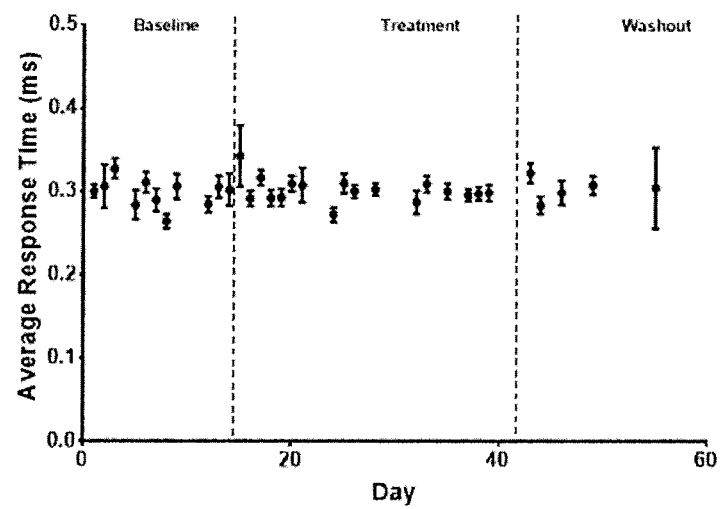

Treatment with 5 g/day Acetyl-DL-Leucine was not associated with significant changes in Psychomotor Vigilance Task performance, relative to the baseline period (0.2983 ms (baseline) vs 0.3025 ms (treatment), p−5105) (FIG. 3A). Test performance was not significantly different during the washout period from either the baseline or on-treatment values (0.3053 ms vs 0.2983/0.3025 ms respectively. Observation of individual day's results from the baseline and treatment period suggest that the values during the treatment period may show relatively little variation (FIG. 3B).

The absence of a significant change in Psychomotor Vigilance Task performance may be due to the subject having a relatively fast baseline reaction speed.

Balance was assessed on the last day of the treatment period. The subject was able to remain balanced for 12 seconds (average of 3 tests). This test was repeated at the end of the washout period. The length of time subject could remain balanced had decreased to 8 seconds (average of 3 tests).

Adverse Effects

None reported.

Example 10

Subject

The subject is a 50-year old male with no apparent dysfunction in cognitive ability or movement/balance.

Study Design

The subject's reaction speed and alertness was assessed via the Mind Metrics App (Psychomotor Vigilance Task, 10 trials per test). The tests were performed daily under comparable conditions. The subject was assessed for 1 week prior to taking acetyl-leucine, which constitutes the baseline period.

From Day 8 onwards, the subject took 5 g Acetyl-DL-Leucine (Tanganil® 500 mg, Pierre Fabre) daily. Medication was taken at least 2 hours after and 30 minutes prior to eating. The 5 g daily dose was taken in 3 separate doses throughout the day-2 g upon waking, 1.5 g prior to lunch and 1.5 g prior to the evening meal. Daily treatments and assessments continued for 2 weeks. The subject then began a 1 week washout period.

Subjective Measurements

The subject reported no difference between on and off medication.

Objective Measurements

Figure 4:
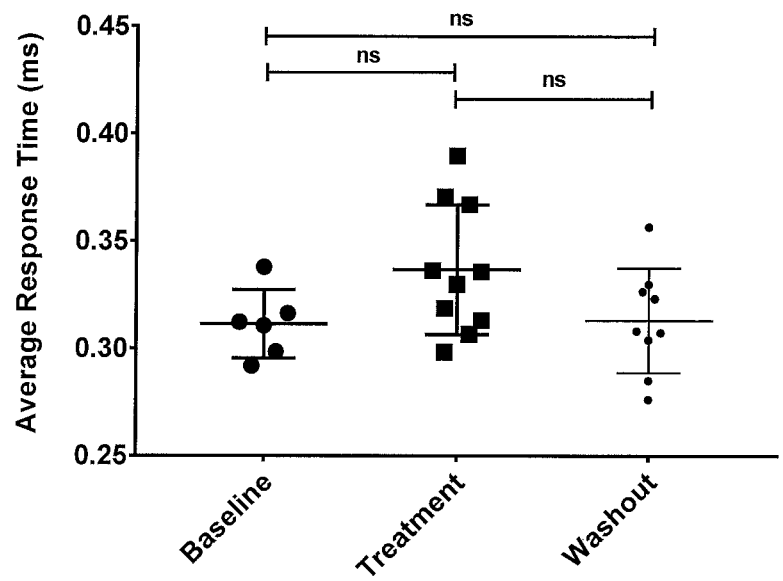
FIG. 4 illustrates the Psychomotor Vigilance Task performance during baseline and treatment period. (A) Data is presented as mean±SD of n=6 (Baseline), 10 (Treatment) or 9 (washout) daily measurements. Determination of statistical significance was performed via 1-way ANOVA with Tukey's correction. (B) Each individual data point is an average of the 10 trials that make up a daily test (mean±SD, n=10). Dashed line indicates division between baseline/on-medication/washout periods.
Figure 4:
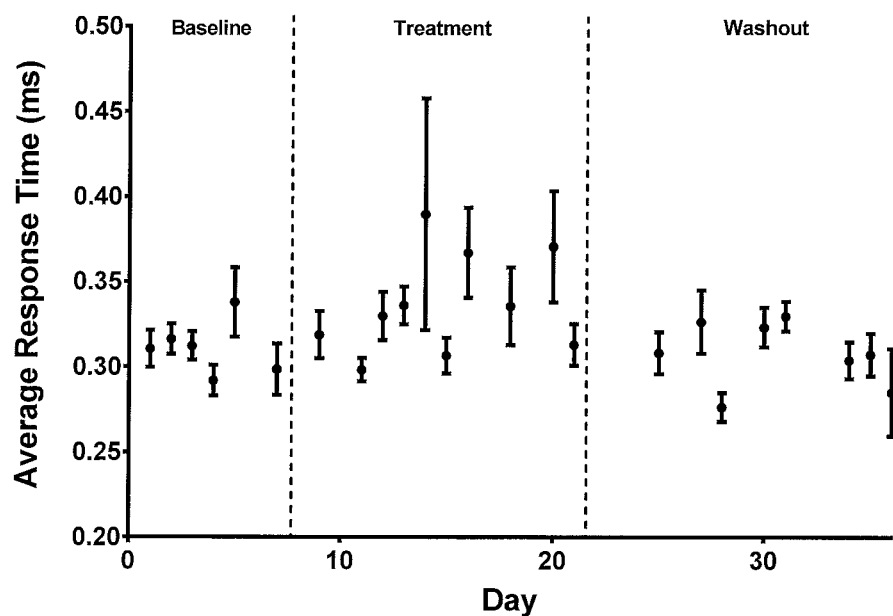

Treatment with 5 g/day Acetyl-DL-Leucine was associated with a small, non-statistically significant decline in Psychomotor Vigilance Task performance, relative to the baseline period (0.3112 ms (baseline) vs 0.3365 ms (treatment), p−0.1545) (FIG. 4A). Test performance was not significantly different during the washout period from either the baseline or on-treatment values (0.3129 ms vs 0.3112/0.3365 ms respectively).

The absence of a significant change in Psychomotor Vigilance Task performance may be due to the subject having a relatively fast baseline reaction speed.

Adverse Effects

None reported.

Example 11

Subject

The subject is a 53-year old male with no apparent dysfunction in cognitive ability or movement/balance.

Study Design

The subject's reaction speed and alertness was assessed via the Mind Metrics App (Psychomotor Vigilance Task, 10 trials per test). The tests were performed daily under comparable conditions. The subject was assessed for 2 weeks prior to taking acetyl-leucine, which constitutes the baseline period.

From Day 15 onwards, the subject took 5 g Acetyl-DL-Leucine (Tanganil® 500 mg, Pierre Fabre) daily. Medication was taken at least 2 hours after and 30 minutes prior to eating. The 5 g daily dose was taken in 3 separate doses throughout the day-2 g upon waking, 1.5 g prior to lunch and 1.5 g prior to the evening meal. Daily treatments and assessments continued for 4 weeks. The subject then began a 2 week washout period.

We measured balancing ability at the end of the treatment period and at the end of the washout period. This assessment required the subject to close their eyes and lift their non-dominant foot around 6 inches off the ground. The subject was then timed to see how long they could remain upright and without significant wobbles. This was repeated three times, and the values averaged.

Subjective Measurements

The subject reported an improvement in general alertness and a shortening of the time required to go from 'asleep' to 'fully awake'.

Objective Measurements

Figure 5:
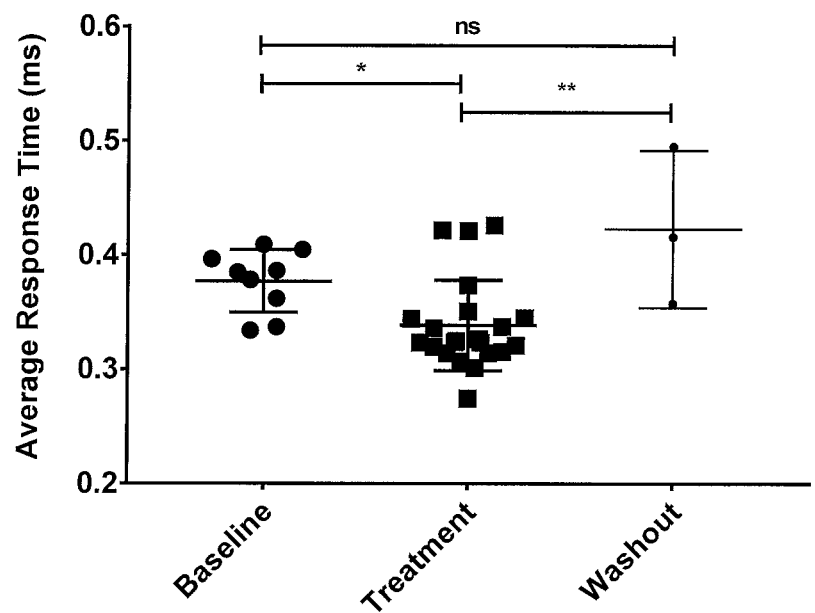
FIG. 5 illustrates the Psychomotor Vigilance Task performance during baseline and treatment period. (A) Data is presented as mean±SD of n=9 (Baseline), 20 (Treatment) or 3 (washout) daily measurements. Determination of statistical significance was performed via 1-way ANOVA with Tukey's correction. (B) Each individual data point is an average of the 10 trials that make up a daily test (mean±SD, n=10). Dashed line indicates division between baseline/on-medication/washout periods.
Figure 5:
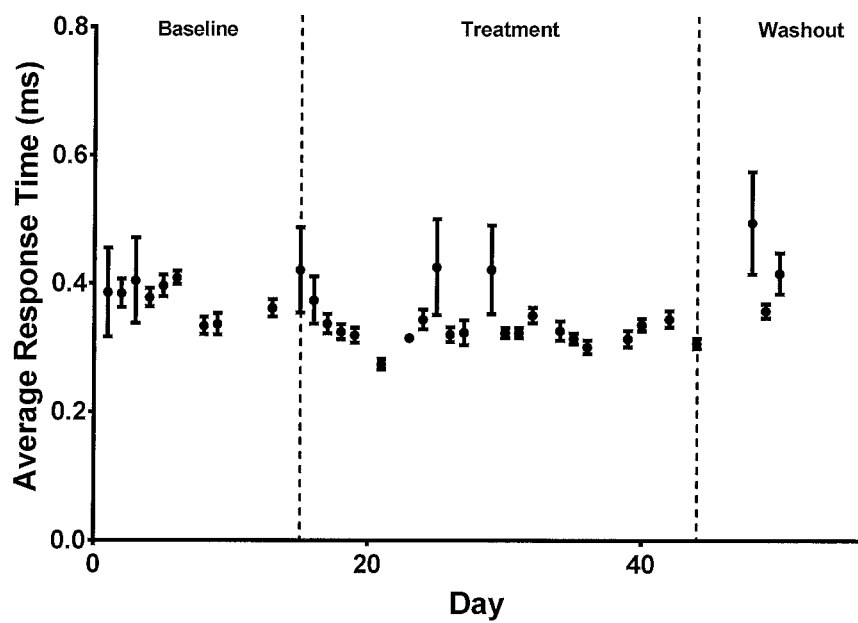

Treatment with 5 g/day Acetyl-DL-Leucine was associated with statistically significant improvements in Psychomotor Vigilance Task performance, relative to the baseline period (0.3771 ms (baseline) vs 0.3385 ms (treatment), p<0.01) (FIG. 5A). Test performance showed a statistically significant decline during the washout period (0.423 ms) relative to on-treatment (0.3385 ms, p<0.01) values, but was not significantly different relative to baseline (0.3771 ms, ns).

Balance was assessed on the last day of the treatment period. The subject was able to remain balanced for 7.9 seconds (average of 3 tests). This test was repeated at the end of the washout period. The length of time subject could remain balanced had decreased to 3.1 seconds (average of 3 tests).

Adverse Effects

None reported.

Example 12

Subject

The subject is a 48-year old woman with no apparent dysfunction in cognitive ability or movement/balance.

Study Design

The subject's reaction speed and alertness was assessed via the Mind Metrics App (Psychomotor Vigilance Task, 10 trials per test). The tests were performed daily under comparable conditions. The subject was assessed for 2 weeks prior to taking acetyl-leucine, which constitutes the baseline period.

From Day 15 onwards, the subject took 5 g Acetyl-DL-Leucine (Tanganil® 500 mg, Pierre Fabre) daily. Medication was taken at least 2 hours after and 30 minutes prior to eating. The 5 g daily dose was taken in 3 separate doses throughout the day-2 g upon waking, 1.5 g prior to lunch and 1.5 g prior to the evening meal. Daily treatments and assessments continued for 4 weeks. Subject then began a 2 week washout period.

Subjective Measurements

The subject reported feeling less tired than usual and taking less time than was usual to go from asleep to fully awake.

Objective Measurements

Figure 6:
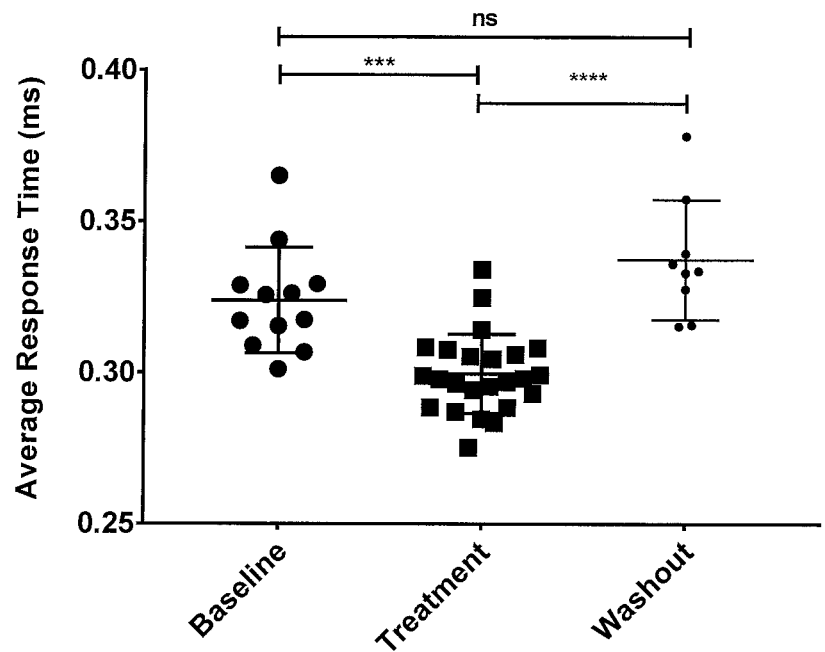
FIG. 6 illustrates the Psychomotor Vigilance Task performance during baseline and treatment period. (A) Data is presented as mean±SD of n=12 (Baseline), 23 (Treatment) or 9 (washout) daily measurements. Determination of statistical significance was performed via 1-way ANOVA with Tukey's correction. (B) Each individual data point is an average of the 10 trials that make up a daily test (mean±SD, n=10). Dashed line indicates division between baseline/on-medication/washout periods.
Figure 6:
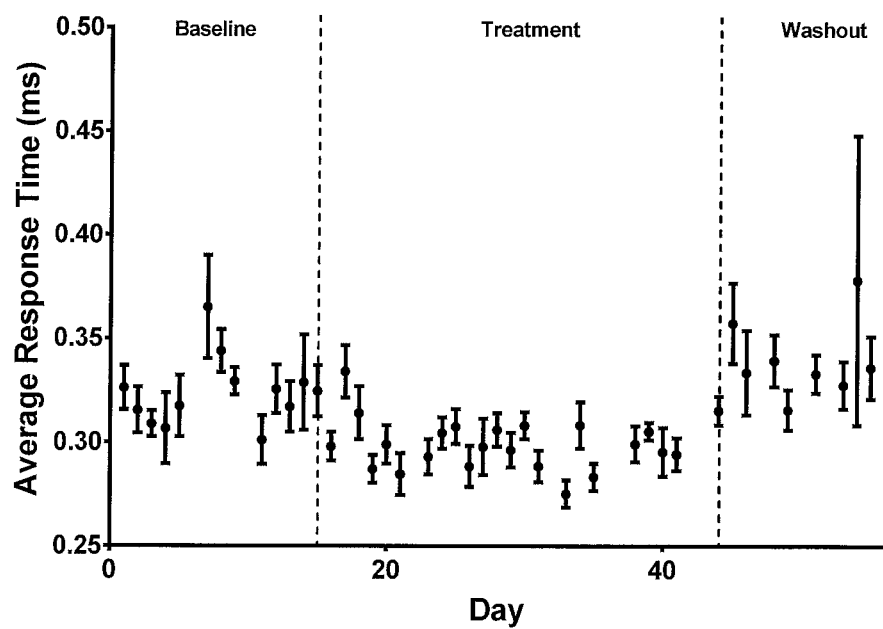

Treatment with 5 g/day Acetyl-DL-Leucine was associated with statistically significant improvements in Psychomotor Vigilance Task performance, relative to the baseline period (0.3238 ms (baseline) vs 0.2996 ms (treatment), p<0.001) (FIG. 6A). Test performance showed a statistically significant decline during the washout period (0.3374 ms) relative to on-treatment (0.2996 ms, p<0.001) values, but was not significantly different relative to baseline (0.3238 ms, ns).

Adverse Effects

None reported.

Taken together, these examples demonstrate the utility of acetyl-leucine in benefiting a range of subjects, including the elderly, in terms of mobility and cognitive function. This is advantageous, since few therapeutic options are currently offered to patients with these very frequent signs and symptoms of ageing. Table 2 summarises the data from Examples 7-12. As can be seen, acetyl-leucine is shown to increase cognitive function and/or mobility. Moreover, those subjects with high baseline reaction times showed most clinical benefit.

TABLE 2

| Age | Gender | Statistically significant improvement in PVT performance on treatment? | Subjective Improvement on treatment? | Average Baseline Reaction Time (ms) | Average On-treatment Reaction Time | % change in Reaction Time | Details on Subjective Improvement | Adverse Effects |
| --- | --- | --- | --- | --- | --- | --- | --- | --- |
| 66 | M | Yes | Yes | 0.444 | 0.307 | −30.85585586 | Improvement in general alertness. Decrease in time taken to go from asleep to fully awake | One episode of mild dizziness. |
| 29 | M | Yes | Yes | 0.3145 | 0.3032 | −3.593004769 | Improvement in general alertness. Decrease in time taken to go from asleep to fully awake. Decrease in anxiety and possible decrease in frequency of depressive episodes. | N/A |
| 55 | F | No | Yes | 0.2983 | 0.3025 | 1.407978545 | Improvement in general alertness. Decrease in time taken to go from asleep to fully awake. | N/A |
| 50 | M | No | No | 0.3112 | 0.3365 | 8.129820051 | N/A | N/A |
| 53 | M | Yes | Yes | 0.3771 | 0.3385 | −10.236011668 | Improvement in general alertness. Decrease in time taken to go from asleep to fully awake | N/A |
| 48 | F | Yes | Yes | 0.3238 | 0.2996 | −7.473749228 | Improvement in general alertness. Decrease in time taken to go from asleep to fully awake | N/A |

The present disclosure is further described by the following numbered paragraphs:

1. Acetyl-leucine, or a pharmaceutically acceptable salt thereof, for use in a method of improving cognitive function, mobility, or cognitive function and mobility in a subject.
2. The acetyl-leucine or pharmaceutically acceptable salt thereof for use according to paragraph 1, wherein the use is in treating an age-related decrease in cognitive function and/or mobility.
3. The acetyl-leucine or pharmaceutically acceptable salt thereof for use according to paragraph 1 or 2, wherein the subject has a decrease in cognitive function associated with ageing and/or a mobility disorder associated with ageing.
4. The acetyl-leucine or pharmaceutically acceptable salt thereof for use according to any one of paragraphs 1-3, wherein the subject is a human aged 40 or over; 50 or over; 60 or over; 70 or over; 75 or over; 80 or over; 85 or over; 90 or over; or 95 or over.

5. The acetyl-leucine or pharmaceutically acceptable salt thereof for use according to any one of paragraphs 1-4, wherein the subject is an elderly subject.

6. The acetyl-leucine or pharmaceutically acceptable salt thereof for use according to any one of paragraphs 1-5, wherein the use is in a method of improving cognitive function in said subject.

7. The acetyl-leucine or pharmaceutically acceptable salt thereof for use according to any any one of paragraphs 1-5, wherein the use is in a method of improving mobility in said subject.

8. The acetyl-leucine or pharmaceutically acceptable salt thereof for use according to any one of paragraphs 1-6, wherein the cognitive function is one or more selected from the group consisting of perception, memory, creation of imagery, awareness, reasoning, thinking and capacity for judgment.

9. Acetyl-leucine, or a pharmaceutically acceptable salt thereof, for use in a method as disclosed in any one of paragraphs 1-8, wherein said acetyl-leucine is in racemate form, in an enantiomeric excess of the L-enantiomer or in an enantiomeric excess of the D-enantiomer.

10. Acetyl-leucine, or a pharmaceutically acceptable salt thereof, for use in a method as disclosed in any one of paragraphs 1-9, wherein said method comprises administering the acetyl-leucine in a dose of between 1.5 g and 10 g, for example between 4 g and 10 g per day.

11. Acetyl-leucine, or a pharmaceutically acceptable salt thereof, for use in a method as disclosed in any one of paragraphs 1-9, wherein said method comprises administering the acetyl-leucine in a dose ranging from 500 mg to 10 g per day, for example ranging from 1 g to 10 g, from 1.5 g to 10 g, from 2 g to 10 g, from 3 g to 10 g, from 4 g to 10 g, from 4.5 g to 10 g, from 1 g to 5 g, from 2 g to 5 g, from 3 g to 5 g, or from 4 g to 5 g per day, optionally by solid oral or liquid oral route.

12. Acetyl-leucine, or a pharmaceutically acceptable salt thereof, for use in a method as disclosed in paragraph 10, wherein said method comprises administering the acetyl-leucine in a dose of more than 4 g to no more than 6 g per day.

13. Acetyl-leucine, or a pharmaceutically acceptable salt thereof, for use in a method as disclosed in any one of paragraphs 10-12, wherein said method comprises administering said dose across two or more administrations.

14. Acetyl-leucine, or a pharmaceutically acceptable salt thereof, for use in a method as disclosed in paragraph 13, wherein said method comprises administering said dose across three administrations.

15. Acetyl-leucine, or a pharmaceutically acceptable salt thereof, for use in a method as disclosed in any one of paragraphs 1-14, wherein said method comprises administering the acetyl-leucine for a treatment duration of two weeks or more.

16. Acetyl-leucine, or a pharmaceutically acceptable salt thereof, for use in a method as disclosed in paragraph 15, wherein said method comprises administering the acetyl-leucine for a treatment duration of seven weeks or more.

17. Acetyl-leucine, or a pharmaceutically acceptable salt thereof, for use in a method as disclosed in any one of paragraphs 1-16, wherein said method comprises administering the acetyl-leucine in a dose of between 4.5 g and 10 g per day, taken across three administrations per day, for a treatment duration of two months or more.

18. Acetyl-leucine, or a pharmaceutically acceptable salt thereof, for use in a method as disclosed in any one of paragraphs 1-16, wherein said method comprises administering the acetyl-leucine in a dose ranging from 4.5 g to 10 g per day, taken across three administrations per day, for a treatment duration of two months or more, for example administering the acetyl-leucine in a dose ranging from more than 4 g to no more than 5 g per day, taken across three administrations per day, for a treatment duration of six months or more.

19. Acetyl-leucine, or a pharmaceutically acceptable salt thereof, for use in a method as disclosed in any one of paragraphs 1-18, wherein the subject is a well elderly subject.

20. Acetyl-leucine, or a pharmaceutically acceptable salt thereof, for use in a method as disclosed in paragraph 19, wherein the subject does not have vertigo, or a neurological or neurodegenerative disease, disorder or condition.

21. Acetyl-leucine, or a pharmaceutically acceptable salt thereof, for use in reducing the time to go from asleep to fully awake.

22. Acetyl-leucine or a pharmaceutically acceptable salt thereof for use in improving balance in a subject, such as where the subject has impaired balance associated with ageing.

23. Acetyl-leucine or a pharmaceutically acceptable salt thereof for use in treating balance disorder associated with ageing.

24. Acetyl-leucine or a pharmaceutically acceptable salt thereof for use in increasing a subject's stability, for example when standing and/or walking, such as where the subject has decreased stability associated with ageing.

25. Acetyl-leucine or a pharmaceutically acceptable salt thereof for use in reducing a subject's unsteadiness whilst walking, such as where the subject has increased unsteadiness associated with ageing.

26. Acetyl-leucine or a pharmaceutically acceptable salt thereof for use in improving gait in subject, such as where the subject has an age-related impairment of gait.

27. Acetyl-leucine or a pharmaceutically acceptable salt thereof for use according to paragraph 26, wherein the use increases gait velocity and/or cadence in said subject.

28. Acetyl-leucine or a pharmaceutically acceptable salt thereof for use in preventing or reducing falling in a subject, such as where the subject has an age-related pre-disposition to falls.

29. Acetyl-leucine or a pharmaceutically acceptable salt thereof for use in increasing reaction speed, such as for use in increasing the speed in which a subject responds to a visual stimulus, for example wherein the subject experiences a decline in reaction speed associated with ageing.

REFERENCES (1) Vibert N, Vidal P P. In vitro effects of acetyl-DL-leucine (tanganil) on central vestibular neurons and vestibulo-ocular networks of the guinea-pig. Eur J Neurosci 2001 February; 13 (4): 735-48.

(2) Ferber-Viart C, Dubreuil C, Vidal P P. Effects of acetyl-DL-leucine in vestibular patients: a clinical study following neurotomy and labyrinthectomy. Audiol Neurootol 2009; 14 (1): 17-25.
(3) Zwergal A, Schlichtiger J, Xiong G, Beck R, Gunther L, Schniepp R et al. Sequential [F]FDG microPET whole-brain imaging of central vestibular compensation: a model of deafferentation-induced brain plasticity. Brain Struct Funct 2014 Oct. 1.
(4) Gunther L, Beck R, Xiong G, Potschka H, Jahn K, Bartenstein P et al. N-acetyl-L-leucine accelerates vestibular compensation after unilateral labyrinthectomy by action in the cerebellum and thalamus. PLOS One 2015; 10 (3): e0120891.
(5) Strupp M, Teufel J, Habs M, Feuerecker R, Muth C, van de Warrenburg B P et al. Effects of acetyl-DL-leucine in patients with cerebellar ataxia: a case series. J Neurol 2013 October; 260 (10): 2556-61.
(6) Pelz J O, Fricke C, Saur D, Classen J. Failure to confirm benefit of acetyl-DL-leucine in degenerative cerebellar ataxia: a case series. J Neurol 2015 May; 262 (5): 1373-5.
(7) Bremova T, Malinova V, Amraoui Y, Mengel E, Reinke J, Kolnikova M et al. Acetyl-dl-leucine in Niemann-Pick type C: A case series. Neurology 2015 Oct. 20; 85 (16): 1368-75.
(8) Becker-Bense S, Feuerecker, R, Xiong G, Feil K, Bartenstein P, Strupp M, Dieterich M. FDG-PET in patients with cerebellar ataxia on-vs. off-treatment with Acetyl-DL-leucine. Abstract EAN 2015.
(9) Smith R. Validation and Reliability of the Elderly Mobility Scale. Physiotherapy 1994; 80 (11): 744-7.

The invention claimed is:

1. A method of treating an age-related decrease in mobility or an age-related decrease in mobility and cognitive function in a subject comprising: administering a therapeutically effective amount of acetyl-leucine or a pharmaceutically acceptable salt thereof to the subject for a treatment duration, wherein the subject does not have a neurological or neurodegenerative disease, disorder, or condition.

2. The method of claim 1, wherein the age-related decrease in mobility is chosen from decreased stability, unsteadiness while walking, senile gait disorder, increase in coefficient of variability of gait velocity or cadence, and predisposition to falls.

3. The method of claim 1, wherein the age-related decrease in mobility is chosen from decreased stability, unsteadiness while walking, senile gait disorder, increase in coefficient of variability of gait velocity or cadence, and predisposition to falls and the age-related decrease in cognitive function is chosen from perception, memory, creation of imagery, awareness, reasoning, thinking and capacity for judgment.

4. The method of claim 1, wherein the acetyl-leucine is administered at least two times a day to achieve a total daily dose of from about 1.5 g to about 10 g.

5. The method of claim 1, wherein the acetyl-leucine is administered at least two times a day to achieve a total daily dose of from about 4.5 g to about 10 g.

6. The method of claim 1, wherein the treatment duration is at least 2 weeks, at least 7 weeks, or continuous treatment.

7. The method of claim 1, wherein the subject is an elderly subject or a well elderly subject.

8. The method of claim 1, wherein the subject is 40 or over, 50 or over, 60 or over, 70 or over, 75 or over, 80 or over, 85 or over, 90 or over, or 95 or over.

9. The method of claim 1, wherein the acetyl-leucine is in racemate form, in an enantiomeric excess of the L-enantiomer, or in an enantiomeric excess of the D-enantiomer.

10. The method of claim 1, wherein the method comprises administering a dose of the acetyl-leucine across two or more administrations.

* * * * *